United States Patent [19]
Toja et al.

[11] Patent Number: 5,204,341
[45] Date of Patent: Apr. 20, 1993

[54] 1-ARYLSULPHONYL-2-PYRROLIDONE DERIVATIVES, THEIR PREPARATION PROCESS AND THE NEW INTERMEDIATES OBTAINED, THEIR USE AS MEDICAMENTS AND THE PHARMACEUTICAL COMPOSITIONS CONTAINING THEM

[75] Inventors: Emilio Toja, Milan; Carla Bonetti, Fontanella; Fernando Barzaghi; Giulio Galliani, both of Monza, all of Italy

[73] Assignee: Roussel Uclaf, Paris, France

[21] Appl. No.: 805,694

[22] Filed: Dec. 11, 1991

[30] Foreign Application Priority Data

Dec. 13, 1990 [IT] Italy ................. 22371 A/90

[51] Int. Cl.$^5$ ............. A61K 31/55; A61K 31/535; A61K 31/495; A61K 31/40; C07D 403/00; C07D 413/00; C07D 207/00

[52] U.S. Cl. .................. 514/212; 514/237.2; 514/252; 514/326; 514/422; 514/424; 514/425; 540/602; 544/141; 544/372; 546/208; 548/518; 548/523; 548/541; 548/542; 548/543

[58] Field of Search ........... 540/602; 546/208; 548/518, 523, 541–543; 514/212, 326, 422, 424, 425, 237.2, 252; 544/141, 372

[56] References Cited

U.S. PATENT DOCUMENTS

| | | | |
|---|---|---|---|
| 3,117,975 | 1/1964 | Bortnick et al. | 514/424 |
| 4,217,130 | 8/1990 | Tsuruta et al. | 71/95 |
| 4,829,079 | 5/1989 | Toja et al. | 514/425 |
| 4,833,156 | 5/1989 | Sakakibara et al. | 514/424 |
| 4,999,372 | 3/1991 | Regnier et al. | 514/422 |
| 5,037,822 | 8/1991 | Toja et al. | 514/425 |
| 5,081,130 | 1/1992 | Galliani et al. | 514/326 |

FOREIGN PATENT DOCUMENTS

| | | |
|---|---|---|
| 0138721 | 4/1985 | European Pat. Off. |
| 63-215624 | 9/1988 | Japan |

OTHER PUBLICATIONS

Chem. Abs., 77 (5):34303f, 1972, Shigezane et al; "3-(Acylamino)-2-Pyrrolidinone Derivatives".

Chem. Abs., 71 (13):61108d, 1969, Stamm; "Aminoethylation With With Aziridines Vi3-Alkoxycarbonyl-2-Pyrrolidinone Compounds".

Chem. Abs., 110:75307d, 1989, Sakakibara et al.

Drugs of the Future, vol. 10, No. 12 (1985), pp. 972–974.

Noller, "Chemistry of Organic Compounds", 2nd Edition (1987), p. 282 (Saunders).

March, "Advanced Organic Chemistry", 3rd Edition (1985), pp. 793–794 (Wiley).

Primary Examiner—Cecilia Tsang
Attorney, Agent, or Firm—Stevens, Davis, Miller & Mosher

[57] ABSTRACT

1-arylsulphonyl-2-pyrrolidone derivatives for treating spasmodic disorders in gastro-enterology, in gynaecology, in obstetrics, in urology; intermediates in the preparation of such products; methods for preparing such products and pharmaceutical preparations containing such products.

14 Claims, No Drawings

1-ARYLSULPHONYL-2-PYRROLIDONE DERIVATIVES, THEIR PREPARATION PROCESS AND THE NEW INTERMEDIATES OBTAINED, THEIR USE AS MEDICAMENTS AND THE PHARMACEUTICAL COMPOSITIONS CONTAINING THEM

The present invention relates to new 1-arylsulphonyl-2-pyrrolidone derivatives, their preparation process and the new intermediates thus obtained, their use as medicaments and the pharmaceutical compositions containing them.

A subject of the invention is the compounds of general formula (I)

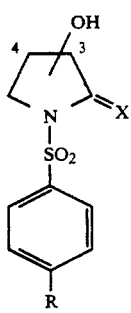

(I)

in which
the OH radical is in position 3 or 4,
X represents an oxygen or sulphur atom,
R in the para position represents a radical

$R_1$ and $R_2$, identical or different from each other, represent a saturated or unsaturated alkyl radical containing up to 8 carbon atoms or form with the nitrogen atom a heterocyclic radical optionally containing another heteroatom, and functional derivatives of the hydroxyl in position 3 or 4, of the compounds of formula (I) which are metabolized in vivo to corresponding hydroxylated derivatives.

The functional derivatives of compounds of formula (I) capable of generating OH "in vivo" can be esters derived from organic acids with linear or branched chains or aromatic chains or also esters derived from an inorganic acid such as phosphoric acid or esters derived from an inorganic acid such as phosphoric acid or sulphuric acid.

By alkyl radical is preferably meant an alkyl radical containing 1 to 8 carbon atoms, for example the following radicals: methyl, ethyl, propyl, isopropyl, butyl, isobutyl, tert-butyl, pentyl, hexyl, cyclopropyl, cyclobutyl, cyclopentyl or cyclohexyl.

By unsaturated alkyl radical is preferably meant an ethenyl, propenyl and butenyl radical.

When $R_1$ and $R_2$ form with the nitrogen atom to which they are linked a heterocyclic radical optionally containing another heteroatom, it is preferably a piperidyl, piperazinyl, hexahydro azepinyl, morpholinyl or pyrrolidinyl radical.

Among the preferred compounds of the invention, there can be mentioned:

the compounds in which the hydroxyl radical is in a free form i.e, the hydroxyl radical is not protected or salified, and notably those in which the hydroxyl radical is in position 4, the compounds in which $R_1$ and $R_2$ form with the nitrogen atom to which they are linked a heterocyclic radical and notably those in which the heterocyclic radical is chosen from 1-piperidinyl and hexahydro-1H-azepin-1-yl radicals, the compounds in which X represents a sulphur atom.

Naturally a more particular subject of the invention is the compounds of which the preparation is given hereafter in the experimental part and quite especially the compounds of Examples 5, 6 and 7.

The compounds of formula (I) have useful pharmacological properties and notably a specific and selective anti-muscarinic activity.

Therefore a subject of the invention is the products of formula (I) as medicaments, useful notably for treating diverse spasmodic disorders in gastro-enterology, in gynaecology, in obstetrics, in urology, in hepatology and in radiology.

A more particular subject of the invention is, as medicaments, the preferred compounds mentioned above, namely the products of Examples 5, 6 and 7.

The usual dosage is variable according to the disease in question, the patient treated and the administration route; it can be comprised between 10 mg and 1 g per day, for example between 30 and 60 mg per day in one or more doses for the product of Example 5 administered by oral route.

Also a subject of the present invention is the pharmaceutical compositions containing as active ingredient at least one product of formula (I). The pharmaceutical compositions of the invention can be solid or liquid and can be presented in the pharmaceutical forms currently used in human medicine, such as for example plain or sugar-coated tablets, capsules, granules, suppositories and injectable preparations; they are prepared according to the usual methods.

The active ingredient or ingredients can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

Also a subject of the invention is a preparation process characterized in that a compound of formula (II):

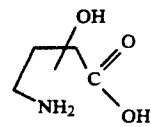

(II)

in which the OH radical is in position 2 or 3, is subjected to the action of a compound of formula (III):

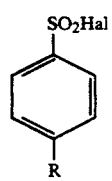

(III)

in which Hal represents a halogen atom and R retains its previous meaning, in order to obtain the compound of formula (IV):

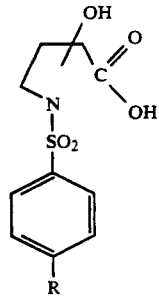
(IV)

which is subjected to the action of a cyclization agent in order to obtain a compound of formula (I$_A$):

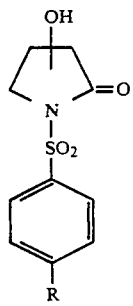
(I$_A$)

in which R has the previous meaning and OH is in position 3 or 4, which is subjected, if appropriate either to the action of a functionalization agent of the hydroxyl radical in order to obtain the corresponding compound of formula (I$_B$):

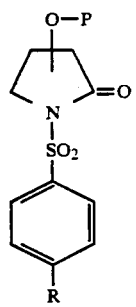
(I$_B$)

in which R has the previous meaning and P represents a functional group of the hydroxyl radical, or to the action of a blocking agent of the hydroxyl in order to obtain the compound of formula (V):

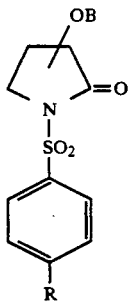
(V)

B representing a protective group of the hydroxyl radical, which is subjected to the action of an agent capable of converting the carbonyl radical to a thiocarbonyl radical in order to obtain the compound of formula (VI):

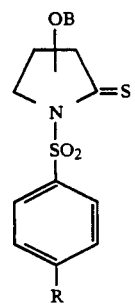
(VI)

which is subjected to the action of a cleavage agent of the protective group of the hydroxyl radical in order to obtain the corresponding compound of formula (I$_C$):

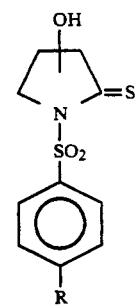
(I$_C$)

in which R has the previous meaning and OH is in position 3 or 4, which is subjected, if appropriate, to the action of a functionalization agent of the hydroxyl group in order to obtain the corresponding compound of formula (I$_D$).

In a preferred method for implementing the process of the invention:

the reaction of the compound of formula (II) with the compound of formula (III) is carried out in the standard conditions of the Schotten Baumann reaction or variations of this, using diazabicyclooctane, an aqueous solution of alkaline hydroxide, or organic bases such as pyridine, the cyclization of the compound of formula (IV) is carried out using cyclization agents chosen from: (CF$_3$CO)$_2$O+CF$_3$CO$_2$Na; (CH$_3$CO)$_2$O+CH$_3$COONa; H$_2$SO$_4$+P$_2$O$_5$; PO$_4$H$_3$; hexamethyl disilazane in the presence of trimethyl-silyl chloride, dicyclohexylcarbodiimide in the presence of pyridine, the blocking of the hydroxyl function in order to obtain the product of formula (V) is carried out by protecting the hydroxyl function with the tert-butyldimethylsilyl group according to the Corey process (J. Am. Chem. Soc. 1972, 94, 6190), or any other silyl derivative as described in "Silicon in Organic Synthesis" Butterworths, London 1981, or also other blocking agents as described in Protective Groups in Organic Synthesis Wiley Interscience N.Y. 1981, the agent capable of converting the carbonyl radical to a thiocarbonyl radical is notably the Lawesson reagent of formula

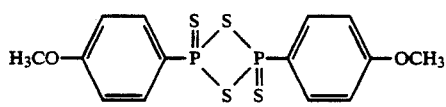

(cf. TETRAHEDRON 41, 2567 (1985) or TETRAHEDRON 41, 5061 (1985)), in an organic solvent such as xylene, toluene, dimethoxyethane, tetrahydrofuran or dioxane.

Other thionation reagents can also be used such as $P_2S_5$; $P_2S_5$-pyridine; $P_2S_5$-TEA; $P_2S_5$-NaHCO$_3$; PCl$_5$-Alk$_2$S$_3$-Na$_2$SO$_4$ or also bis(tricyclohexyltin) sulphide in the presence of boron trichloride.

The cleavage of the protective group of the hydroxyl function is carried out, for example, using trimethylsilyl trifluoromethane sulphonate in an inert organic solvent according to the process of V. Bon and J. Villarasa (Tetrahedron Letters 1990, 31, 567-568) or also using tetrabutylammonium fluoride in tetrahydrofuran, the functional derivative ($I_B$) or ($I_D$) can be obtained according to standard conditions known to a man skilled in the art. There can be used for example as esterification agent, an acid halide, preferably a carboxylic acid chloride such as acetic, pivalic, hemisuccinic, benzoic, alkyl- or dialkylamino acetic, or nicotinic acid, or also a phosphoric or sulphuric acid derivative.

Also a subject of the invention is a variant of the process described previously, characterized in that a compound of formula (VII):

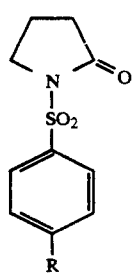

(VII)

in which R retains its previous meaning, is subjected to the action of a base in order to obtain the enolate of formula (VIII):

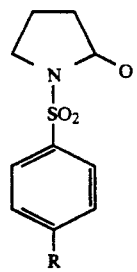

(VIII)

which is subjected to the action of an oxidizing agent in order to obtain the corresponding compound of formula (I) in which the hydroxyl is free, then if desired the carbonyl radical is functionalized or if desired converted to a thiocarbonyl radical as indicated previously, then if desired the compound obtained is functionalized.

In a preferred method for implementing the process of the invention:

the base used is chosen from lithium, sodium or potassium (bistrimethylsilyl) amide, or also other bases such as lithium diisopropylamide, and the operation is carried out at low temperature, in an inert solvent such as tetrahydrofuran, ether, dioxane, benzene, toluene.

The oxidizing agent used is 2-sulphonyl oxaziridine (cf Organic Synthesis Vol. 66, 203-210 (1988)). Oxodiperoxy-molybdenum (pyridine) hexamethyl phosphoryltriamide can also be used, or organic peracids such as metachloroperbenzoic acid or organic peroxides such as bis(trimethylsilyl) peroxide or dibenzylperoxydicarbonate.

The products of formula (VII) used as starting products are described and claimed in the European Patent No. 0335758. The products obtained during the implementation of the process of the invention and its variant are new and are themselves a subject of the present invention: the products of formulae (IV), (V), (VI) and (VIII) are concerned.

The following examples illustrate the invention without however limiting it.

EXAMPLE 1:

1-[[4-(diethylamino)-phenyl]sulphonyl]-4-hydroxy-2-pyrrolidinone

Stage A:

4-[[[4-(diethylamino)-phenyl]-sulphonyl]-amino]-3-hydroxy butanoic acid

A solution of 2.47 g 4-diethyl aminobenzenesulphonyl chloride in 3.4 cm$^3$ of acetone is added to a solution of 1.19 g of 3-hydroxy-4-amino butanoic acid and 2.24 g of 1,4- diazabicyclo[2.2.2]octane (DABCO) in 10 cm$^3$ of water: immediate exothermic reaction. The mixture is agitated for 3 hours. The acetone is eliminated under reduced pressure then 5 cm$^3$ of 2N hydrochloric acid is added at 0° C. Extraction is carried out once with 150 cm$^3$ of chloroform and then twice with 100 cm$^3$ of chloroform, the extracts are washed with water, dried and evaporated to dryness under reduced pressure. 3.4 g of desired product is obtained.

Stage B:
1-[[4-(diethylamino)-phenyl]-sulphonyl]-4-hydroxy-2-pyrrolidinone 50 cm³ of trifluoroacetic anhydride and 4 g of sodium trifluoroacetate are added to a suspension of 11.6 g of the product obtained as in Stage A in 100 cm³ of benzene, and the mixture is taken to reflux for 18 hours. After evaporation to dryness, the residue is taken up in methylene chloride, the insoluble part is filtered out and evaporated to dryness under reduced pressure. The insoluble part is dissolved in water and extraction is carried out with chloroform in order to obtain 1.8 g of cyclized product. After evaporation of the chloroform, 17.19 g of the trifluoroacetic salt of the trifluoroacetate of the expected product is obtained. Neutralization is carried out with 20 cm³ of a saturated solution of sodium bicarbonate, followed by taking up in 100 cm³ of methanol, agitating for one hour, adding water and filtering. After crystallization from ethanol, 5.23 g of crude product is obtained and 2.5 g of additional product is obtained from the mother liquors. After chromatography on silica (eluant: ethyl acetate - hexane (8-2)), 6.25 g of desired product is obtained, M.p.=165° C., recrystallized from ethyl acetate, and 1.48 g of product is obtained containing a double bond in position 3,4 of the pyrrolidinone.

| Analysis for: $C_{14}H_{20}N_2O_4S$. | | M.W.: 312.39 | | |
|---|---|---|---|---|
| Calculated: | C % 53.83 | H % 6.45 | N % 8.97 | S % 10.26 |
| Found: | 53.57 | 6.53 | 8.96 | |

EXAMPLE 2:
1-[[4-(dimethylamino)-phenyl]-sulphonyl]-4-(2,2-dimethyl-1-oxo-propoxy)-2-pyrrolidinone 0.41 g of 1,4-diazabicyclo [2.2.2]octane (DABCO) is added at 3° C. to a solution of 1 g of [1-(4-diethylamino-benzenesulphonyl)-4-hydroxy-pyrrolidin-2-one] in 20 cm³ of methylene chloride, and then 0.43 g of pivaloyl chloride in solution in 3 cm³ of methylene chloride is added slowly, and the whole mixture is left at ambient temperature for 16 hours. Another equivalent of pivaloyl chloride and DABCO is added, the mixture is left at ambient temperature for 4 hours, brought to dryness, the residue is taken up in ethyl acetate, washed with water (at a pH of about 6), followed by filtering and bringing to dryness under reduced pressure, and the residue is chromatographed on silica (eluant: ethyl acetate - hexane 4-1). 0.6 g of expected crude product and 0.3 g of product containing a double bond in position 3,4 of the pyrrolidinone are obtained. The crude product is added to a previous preparation in order to obtain, after recrystallization from an ethyl acetate - hexane mixture (3-50), 0.86 g of the desired product. M.p.=117-118° C.

EXAMPLE 3:
1-[[4-(diethylamino)-phenyl]-sulphonyl]-4-hydroxy-2pyrrolidine thione

Stage A:
1-[[4-(diethylamino)-phenyl]-sulphonyl]-4-[(1,1-dimethyethyl)-dimethyl tert-butylsilyloxy]-2-pyrrolidinone 0.6 g of dimethyltertbutyl chlorosilane is added in 4 or 5 lots to a mixture of 1 g of [1-(4-diethylamino benzene sulphonyl -yl)-4-hydroxy-pyrrolidin-2-one], 550 mg of imidazole and 3 cm³ of dimethylformamide. After 3 hours at ambient temperature, the solvent is eliminated under reduced pressure, the residue is taken up in water, extraction is carried out three times with 20 cm³ of methylene chloride, the extracts are dried and evaporated to dryness under reduced pressure. The residue is chromatographed on silica (eluant: ethyl acetate - hexane 1-1), and 1.31 g of desired product is obtained. M.p. =90-92° C.

| Analysis for: $C_{20}H_{34}N_2O_4S$ Si. | | | M.W. = 426.65 | | |
|---|---|---|---|---|---|
| Calculated: | C % 56.30 | H % 8.03 | N % 6.57 | S % 7.52 | Si % 6.58 |
| Found: | 56.12 | 7.99 | 6.47 | | |

Stage B:
1-[[4-(diethylamino)-phenyl]-sulphonyl]-4-[(1,1-dimethyethyl) -dimethylsilyloxy]-2-pyrrolidine thione A mixture of 3.14 g of the product obtained in Stage A above 1.55 g of Lawesson reagent in 40 cm³ of toluene is taken to reflux for 4 hours. The solvent is evaporated under reduced pressure and the residue is chromatographed on silica (eluant: ethyl acetate - hexane 3-7). 2.45 g of desired product is obtained. M.p.=136° C. (after dissolution in ethyl acetate, filtration, evaporation to dryness, impasting in hexane).

| Analysis for: $C_{20}H_{34}N_2O_3S_2Si$. | | | M.W. = 442.72 | | |
|---|---|---|---|---|---|
| Calculated: | C % 54.26 | H % 7.74 | N % 6.33 | S % 14.49 | Si % 6.34 |
| Found: | 54.13 | 7.73 | 6.28 | | |

Stage C:
1-[[4-(diethylamino)-phenyl]-sulphonyl]-4-hydroxy-2-pyrrolidine thione 30 cm³ of sodium bicarbonate is added at −20° C. over one hour to a solution of 1.3 g of 1-[[4-(diethylamino)-phenyl]-sulphonyl]-4-[(1,1-dimethylethyl)-dimethylsilyloxy]-2-pyrrolidine thione obtained above, in 30 cm³ of methylene chloride. The mixture is agitated for 16 hours at ambient temperature, decanted, extracted with methylene chloride, the extracts are dried and evaporated to dryness. After crystallization from a chloroform - hexane mixture, 700 mg of the desired product is obtained. M.p=149-150° C.

| Analysis for: $C_{14}H_{20}N_2O_3S_2$. | | M.W. = 328.46 | | |
|---|---|---|---|---|
| Calculated: | C % 51.20 | H % 6.14 | N % 8.53 | S % 19.52 |
| Found: | 50.66 | 6.08 | 8.39 | |

EXAMPLE 4:

4-hydroxy-1-[[4-(1-piperidinyl)-phenyl]-sulphonyl]-2-pyrrolidinone

Stage A:

[3-hydroxy-4-[[4-(1-piperidinyl)-phenyl]-sulphonyl]-amino]butanoic acid 2.34 g of [4-(piperidinyl)-benzenesulphonyl]chloride and 15 cm³ of acetone are added to a solution of 1.07 g of 3-hydroxy-4-amino butanoic acid and 2.08 g of 1,4-diazabicyclo[2.2.2]-octane (DABCO) in 10 cm³ of water. The resultant mixture is agitated for 6 hours at ambient temperature and left at rest for 16 hours. The acetone is eliminated, the residue is cooled down to 0° C. and 4.5 cm³ of 2N hydrochloric acid is added. Extraction is carried out five times with 60 cm³ of chloroform, the extracts are dried and evaporated to dryness under reduced pressure. 3 g of the expected product is obtained which is used as it is for the following stage.

Stage B:

4-hydroxy-1-[[4-(1-piperidinyl)-phenyl]-sulphonyl]-2-pyrrolidinone 3 g of the product obtained in Stage A above, 15 cm³ of trifluoroacetic anhydride and 1.5 g of sodium trifluoro-acetate in 50 cm³ of benzene are taken to reflux for 3 hours. The mixture is evaporated to dryness and the residue is taken up in successive additions of 60 cm³ of methanol and 55 cm³ of a 5% solution of sodium bicarbonate in methanol. Agitation is carried out for 3 hours at ambient temperature, the methanol is evaporated off at 30° C. and concentration is carried out to a volume of 30 cm³. Extraction is carried out with methylene chloride, the extracts are dried and evaporated to dryness under reduced pressure. 1.7 g of product is collected which is chromatographed on silica (eluant: ethyl acetate - hexane (4-1)). 0.95 g of expected product is obtained, precipitated from ethyl acetate with hexane. M.p.=158–159° C.

| Analysis for: $C_{15}H_{20}N_2O_4S$. | | | | M.W. = 324.40 | | | |
|---|---|---|---|---|---|---|---|
| Calculated: | C % 55.53 | H % 6.21 | N % 8.64 | O % 19.73 | Si % 9.88 | | |
| Found: | 55.36 | 6.17 | 8.61 | | | | |

EXAMPLE 5:

4-hydroxy-1-[[(4-(1-piperidinyl)-phenyl]-sulphonyl]-2-pyrrolidine thione

Stage A:

4-[[(1,1-dimethylethyl)-dimethylsilyloxy]-1-[[4-(1-piperidinyl) -phenyl]-sulphonyl]-2-pyrrolidinone 150 g of tertbutyl dimethylchlorosilane is added in batches to a solution of [1-(4-piperidin-1-yl)-benzenesulphonyl-4-hydroxy pyrrolidine-2-one] and 1.37 g of imidazole in 10 cm³ of dimethylformamide, and the mixture is agitated for 3 hours at ambient temperature. The solvent is evaporated off under reduced pressure, the residue is taken up in a small amount of water and extraction is carried out with ethyl acetate, the extracts are dried and evaporated to dryness under reduced pressure. The residue is chromatographed on silica (eluant: ethyl acetate - n-hexane (2-3)), and 2.88 g of the desired product is obtained. M.p.=111–112° C.

| Analysis for: $C_{21}H_{34}N_2O_4S$ Si. | | | | M.W. = 438.67 | |
|---|---|---|---|---|---|
| Calculated: | C % 57.50 | H % 7.81 | N % 6.39 | S % 7.31 | Si % 6.40 |
| Found: | 57.66 | 7.85 | 6.54 | | |

Stage B:

4-[[(1,1-dimethylethyl)-dimethylsilyloxy]-1-[[4-(1-piperidinyl) -phenyl]-sulphonyl]-2-pyrrolidine thione A mixture of 2.7 g of the product obtained in Stage A above with 1.55 g of Lawesson reagent in 25 cm³ of toluene is taken to reflux for 3 hours 15 minutes. After cooling, the solvent is eliminated and the residue is chromatographed on silica (eluant: ethyl acetate - n-hexane (3-7)). 2.32 g of the desired product is obtained. M.p.=152.5–153° C. after dissolution in ethyl acetate and precipitation with hexane.

| Analysis for: $C_{21}H_{34}N_2O_3S_2$ Si. | | | | M.W. = 454.73 | |
|---|---|---|---|---|---|
| Calculated: | C % 57.47 | H % 7.54 | N % 6.16 | S % 14.10 | Si % 6.18 |
| Found: | 57.71 | 7.62 | 6.22 | | |

Stage C:

4-hydroxy-1-[[(4-(1-piperidinyl)-phenyl]-sulphonyl]-2-pyrrolidine thione 2.44 cm³ of trimethylsilyl trifluoromethanesulphonate is added to a solution of 2.2 g of the product obtained in Stage B above in 25 cm³ of methylene chloride, cooled down to −20° C. The mixture is maintained at −20° C. for one hour 30 minutes, 20 cm³ of a 5% solution of sodium bicarbonate and a spatula tip of sodium bicarbonate sticks are added at −10° C. in order to obtain a pH of about 8. The mixture is left to return to ambient temperature and after 2 hours the aqueous phase is extracted with methylene chloride, the extracts are dried and brought to a reduced volume, precipitated with hexane and 1.4 g of desired product is obtained.

M.p.=168–169° C.

| Analysis for: $C_{15}H_{20}N_2O_3S_2$. | | | | M.W. = 340.47 |
|---|---|---|---|---|
| Calculated: | C % 52.92 | H % 5.92 | N % 8.23 | S % 18.84 |
| Found: | 52.61 | 5.83 | 8.16 | |

EXAMPLE 6:

1-[[4-(hexahydro-1H-azepin-1-yl)-phenyl]-sulphonyl]-4-hydroxy-pyrrolidine

Stage A:
4-[[[4-(hexahydro-1H-azepin-1-yl)-phenyl]-sulphonyl]-amino]-3-hydroxy butanoic acid 4.1 g of (4-hexahydro-azepin-1-yl-benzenesulphonyl) chloride then 12 cm³ of acetone are added to a solution of 1.4 g of 3-hydroxy-4-amino butanoic acid and 3.36 g of 1,4-diazabicyclo [2.2.2]octane (DABCO) in 18 cm³ of water. Agitation is carried out for 6 hours at ambient temperature, the acetone is evaporated off, the residue is cooled down to 0° C. and 7.5 cm³ of 2N hydrochloric acid is added. Extraction is carried out with chloroform, the extracts are dried and evaporated to dryness. 6.3 g of desired product is obtained, used as it is for the following stage.

Stage B:
1-[[4-(hexahydro-1H-azepin-1-yl)-phenyl]-sulphonyl]-4-hydroxy-pyrrolidinone 6.3 g of the product obtained in Stage A above, 30 cm³ of trifluoroacetic anhydride and 6.3 g of sodium trifluoro-acetate are agitated under reflux for 12 hours. The mixture is evaporated to dryness, cooled down and the residue is taken up immediately in 120 cm³ of a 5% solution of sodium bicarbonate then in 350 cm³ of methanol. Agitation is carried out for 3 hours at ambient temperature, the mixture is concentrated to a reduced volume at 30° C. then extracted with methylene chloride, the extracts are dried and evaporated. The residue is chromatographed on silica (eluant: ethyl acetate - hexane (8-2)) after crystallization from ethanol, 2.1 g of desired product, M.p.=170–172° C., and 0.3 g of the corresponding delta-3,4 derivative are obtained.

| Analysis for: $C_{16}H_{22}N_2O_4S$ M.W. = 338.43 | | | | |
|---|---|---|---|---|
| Calculated: | C % 56.79 | H % 6.55 | N % 8.29 | S % 9.47 |
| Found: | 56.55 | 6.59 | 8.38 | |

EXAMPLE 7

1-[[4-(hexahydro-1H-azepin-1-yl)-phenyl]-sulphonyl]-4-hydroxy pyrrolidine thione

Stage A:
4-[[(1,1-dimethylethyl)-dimethylsilyloxy]-1-[[4-(hexahydro-1H-azepin-1-yl)-phenyl]-sulphonyl]-4-hydroxy-pyrrolidinone 1.38 g of tertbutyl dimethylchlorosilane is added in batches to a solution of 2.5 g of [1-(4-(hexahydro-1H-azepin-1-yl)benzenesulphonyl-4-hydroxy-pyrrolidin-2-one] and 1.27 g of imidazole in 10 cm³ of dimethylformamide, and the mixture is agitated for one hour 30 minutes. The solvent is evaporated off, the residue is taken up in 10 cm³ of water and extraction is carried out with methylene chloride, the extracts are dried and evaporated to dryness. After chromatography on silica (eluant: ethyl acetate - hexane 4-6) 3.1 g of desired product is obtained. M.p.=121° C.

| Analysis for: $C_{22}H_{36}N_2O_4S$ Si M.W. = 452.69 | | | | | |
|---|---|---|---|---|---|
| Calculated: | C % 58.37 | H % 8.02 | N % 6.19 | S % 7.08 | Si % 6.20 |
| Found: | 58.58 | 7.91 | 6.28 | | |

Stage B:
4-[[(1,1-dimethylethyl)-dimethylsilyloxy]-1-[[4-(hexahydro-1H-azepin-1-yl)-phenyl]-sulphonyl]-2-pyrrolidine thione A mixture of 3 g of the product obtained in the previous stage and 1.61 g of Lawesson reagent in 30 cm³ of toluene is taken to reflux for 4 hours 30 minutes. The solvent is eliminated and the residue is chromatographed on silica (eluant: ethyl acetate-hexane 3-7). 2.5 g of expected product is obtained. M.p.=135–136° C. (after impasting in hexane).

| Analysis for: $C_{22}H_{36}N_2O_3S_2Si$ M.W. = 452.69 | | | | | |
|---|---|---|---|---|---|
| Calculated: | C % 56.37 | H % 7.74 | N % 5.98 | S % 13.68 | Si % 5.99 |
| Found: | 56.63 | 7.69 | 5.91 | | |

Stage C:
1-[[4-(hexahydro-1H-azepin-1-yl)-phenyl]-sulphonyl]-4-hydroxy-pyrrolidine thione 2.6 cm³ of trimethylsilyl triflate is added at −20° C. to a solution of 2.3 g of the product obtained in the previous stage in 25 cm³ of methylene chloride. The mixture is agitated for one hour 30 minutes cold, then at −10° C., 20 cm³ of a 5% solution of sodium bicarbonate and a small amount of sodium bicarbonate in sticks is added to adjust the pH to about 8. Agitation is carried out for 30 minutes at ambient temperature, the aqueous phase is separated out and extracted with methylene chloride, dried and evaporated to dryness under reduced pressure. The residue is dissolved in chloroform, filtered and precipitated by the addition of n-hexane, and 1.5 g of desired product is obtained M.p.=138–139° C.

| Analysis for: $C_{16}H_{22}O_3S_2$ M.W. = 354.49 | | | | |
|---|---|---|---|---|
| Calculated: | C % 54.21 | H % 6.26 | N % 7.90 | S % 18.09 |
| Found: | 54.02 | 6.21 | 7.86 | |

EXAMPLE 8

4-(benzyloxy)-1-[[(4-diethylamino)-phenyl]-sulphonyl]-2-pyrrolidinone 2.27 cm³ of a 1.6M solution of butyllithium in hexane is added at −65° C. to a solution of 1.03 g of [1-(4-diethylamino-benzene sulphonyl)-4-hydroxy pyrrolidin-2-one] in 20 cm³ of tetrahydrofuran. The mixture is left for 20 minutes at −70° C. and 0.51 g of benzoyl chloride in 3 cm³ of tetrahydrofuran is added slowly then the resultant medium is left to return to ambient temperature and agitated for 30 minutes. After evaporating to dryness, the residue is taken up in water, extraction is carried out with ethyl acetate, the solvent is eliminated and the residue is chromatographed on silica (eluant: ethyl acetate - n-hexane 1-1). 1.1 g of crude product is obtained containing a small amount of delta-3,4 derivative which is crystallized from ethyl acetate-hexane. 0.95 g of desired product is obtained. M.p. =118–120° C.

| Analysis for: $C_{21}H_{24}N_2O_5S$ M.W. = 416.50 | | | | |
|---|---|---|---|---|
| Calculated: | C % 60.56 | H % 5.81 | N % 6.73 | S % 7.70 |
| Found: | 60.66 | 5.93 | 6.75 | |

EXAMPLE 9

[1-[[4-(diethylamino)-phenyl]-sulphonyl]-2-oxo-pyrrolidin-4-yl di-(tertbutyl)phosphate 0.75 g of [di-tertbutyl-N,N-diethyl phosphoramidate](Synthesis (1988) 142–144) and in one lot 0.76 g of tetrazole are added to a suspension of 1.03 g of [1-(4-diethylamino-benzenesulphonyl) -4-hydroxy pyrrolidine-2-one] in 10 cm³ of tetrahydrofuran, and the mixture is agitated for 30 minutes at ambient temperature and cooled down to −50° C. 1.38 g of metachloroperbenzoic acid at 50–60% in 7 cm³ of methylene chloride is added rapidly while maintaining the temperature below 0° C. The temperature is allowed to return to ambient and agitation is carried out for 10 minutes; 10 cm³ of a 10% sodium bisulphite solution is added and after 10 minutes at ambient temperature, 70 cm³ of diethyl ether is added. After decanting, the organic phase is washed twice with 20 cm³ of a 10% solution of sodium bisulphite then twice with 5% sodium bicarbonate, dried and evaporated to dryness under reduced pressure. The residue is chromatographed on silica (eluant: chloroform - acetone 4-1) and 1 g of desired product is obtained.

Analysis for: $C_{22}H_{37}N_2O_7PS$. M.W.=504.59
Calculated: C % 52.37. H % 7.39. N % 5.55. P % 6.14. S % 6.35

EXAMPLE 10:

[1-[[4-(diethylamino) phenyl]-sulph-onyl]-2-oxopyrrolidin-4-yl phosphate

The mixture of 1.51 g of the product obtained in Example 9 with 30 cm³ of N hydrochloric acid in dioxane is agitated for 4 hours. The mixture is evaporated to dryness, the residue is taken up in a small amount of water and extracted with ethyl acetate. The extracts are dried and then evaporated to dryness under reduced pressure, and 0.99 g of crude product is obtained containing a small amount of the corresponding delta-3,4 derivative which is impasted in ethyl acetate and in this way 0.80 g of the desired product is collected. M.p. =89–90° C.

| Analysis for: $C_{14}H_{21}N_2O_7PS$ M.W. = 392.37 | | | | | |
|---|---|---|---|---|---|
| Calculated: | C % 42.86 | H % 5.39 | N % 7.14 | P % 7.89 | S % 8.17 |
| Found: | 42.91 | 5.48 | 7.27 | | |

EXAMPLE 11:

1-[[4-(diethylamino)-phenyl]-sulphonyl]-3-hydroxy-2-pyrrolidinone 31.2 cm³ of a molar solution of hexamethyldisilylazane lithium salt is added to a solution of 9.3 g of [1(4-diethyl-aminophenylsulphonyl) -pyrrolidin-2-one]prepared as in the European Patent Application No. E.P.A. 0,335,758 in 280 cm³ of tetrahydrofuran cooled down to −78° C., maintaining the temperature below −70° C. Agitation is carried out for one hour at −78° C. then 12.3 g of 2sulphonyloxaziridine (Org. Synthesis 66 203–210 (1988)) is added in one lot and followed by agitation for 2 hours at −78° C. The mixture is left to return to −5° C. then cooled down to −40° C. and 150 cm³ of a saturated aqueous solution of ammonium chloride is added; the temperature is left to return to ambient and 130 cm³ of a saturated solution of sodium chloride is added, the aqueous phase is washed with chloroform, dried and evaporated to dryness under reduced pressure. The residue is chromato-graphed on silica (eluant: ethyl acetate - hexane (1-1)) and 2.6 g of product is obtained which is recrystallized twice from isopropanol in order to collect 1.8 g of desired product. M.p. =164–165° C.

| Analysis for: $C_{14}H_{20}N_2O_4S$ M.W. = 312.39 | | | |
|---|---|---|---|
| Calculated: | C% 53.83 | H % 6.45 | N % 8.97 |
| Found: | 53.91 | 6.50 | 8.94 |

EXAMPLE 12

1-[[4-(diethylamino)-phenyl]-sulphonyl]-3-hydroxy-2-pyrrolidin-2thione

Operating as in Example 3, starting with the compound obtained in the above example, the desired product was prepared.

Operating as in Example 8, using suitable reagents, the compounds of the following examples were obtained:

EXAMPLE 13

1-[[(4-diethylamino)-phenyl]-sulphonyl]-2-pyrrolidinone-4-yl 3methoxycarbonyl propanoate

| Analysis for: $C_{19}H_{26}N_2O_7S$ M.W. = 426.49 | | | |
|---|---|---|---|
| Calculated: | C% 53.51 | H % 6.14 | N % 6.57 |
| Found: | 53.68 | 6.12 | 6.42 |

EXAMPLE 14

1-[[(4-diethylamino)-phenyl]-sulphonyl]-2-pyrrolidinone-4-yl benzyl carbonate

M.p.=105–106° C.

| Analysis for: $C_{22}H_{26}N_2O_6S$ M.W. = 446.53 | | | |
|---|---|---|---|
| Calculated: | C% 59.18 | H % 5.87 | N % 6.27 |
| Found: | 59.33 | 5.78 | 6.16 |

EXAMPLE 15

4-[(3-pyridin)-carbonyloxy]-1-[[(4-diemthylamino)-phenyl]-sulphonyl]2-pyrrolidinone M.p.=134–135° C.

| Analysis for: $C_{20}H_{23}N_3O_5S$ | | M.W. = 417.49 | |
|---|---|---|---|
| Calculated: | C% 57.54 | H% 5.55 | N% 10.07 |
| Found: | 57.75 | 5.67 | 10.18 |

EXAMPLE 16:

4-acetoxy-1-[[(4-diethylamino)-phenyl]-sulphonyl]-2-pyrrolidinone

M.p.=92–94° C.

| Analysis for: $C_{16}H_{22}N_2O_5S$ | | M.W. = 354.43 | |
|---|---|---|---|
| Calculated: | C% 54.22 | H% 6.26 | N% 7.90 |
| Found: | 54.45 | 6.37 | 8.03 |

EXAMPLES OF PHARMACEUTICAL COMPOSITIONS a) Tablets were prepared corresponding to the following formula:

| Product of Example 5 | 10 mg |
|---|---|
| Excipient sufficient quantity for a tablet completed at | 300 mg |

(Detail of excipient: lactose, wheat starch, treated starch, rice starch, magnesium stearate, talc).

b) Capsules were prepared corresponding to the following formula:

| Product of Example 7 | 20 mg |
|---|---|
| Excipient sufficient quantity for a capsule completed at | 300 mg |

(Excipient: talc, magnesium stearate, aerosil).

BIOCHEMICAL AND PHARMACOLOGICAL STUDIES

1) Bonding With Different Cerebral Receptors a) Muscarinic receptor 1

Its preparation is carried out from cortex removed from the brains of male rats weighing 150 to 200 g (Iffa Credo) ground up in a Polytron in a 10 mM Na/K pH 7.4 buffer. After incubation (0.5 ml aliquots of homogenate) for 60 minutes at 25° C. in the presence of 0.25 nM of $^3H$ pirenzepine either on its own, or with the product to be tested, or with an excess of pirenzepine at $10^{-5}M$ (in order to determine the non-specific fixed radioactivity), the incubates are cooled down and filtered.

The filtration is carried out on Whatman GF/C filters prewashed in a 0.05% polyethylene imine solution. The filters are rinsed with 3×5 ml of 10 mM Na/K pH 7.4 phosphate buffer, then measurements are carried out by liquid scintillation.

b) Muscarinic receptor 2

The preparation is carried out from the brains of male rats weighing 150 to 200 g (Iffa Credo).

The brains are ground up (Teflon-glass) in a 0.32 M sucrose solution. The homogenate is centrifuged for 10 minutes at 1000 g (0−4° C.).

The supernatant obtained is collected and centrifuged again at 30000 g for 15 minutes (0−4° C.).

The deposit is put in suspensions in a 50 mM Tris pH 7.5 buffer and the new homogenate is centrifuged again at 30000 g for 15 minutes (0−4° C.).

After elimination of the supernatants, the deposits can be used immediately or kept for up to one month at −30° C.

For one experiment the deposits are firstly defrosted, if necessary, at ambient temperature and put in suspension using a Dounce grinder in a 50 mM Tris pH 7.5 buffer. 2 ml aliquots are incubated for 60 minutes at 25° C. in the presence of 0.3 nM of $^3H$ quinuclidinyl benzylate either on its own, or with the product to be tested, or with benzatropine at $10^{-5}M$ in order to determine the non-specific fixed radioactivity.

At the end of the incubation, the tubes of incubate are cooled down to 4° C. and the incubate is filtered rapidly on Whatman GF/C filters. The filters are rinsed with 3×5 ml of 50 mM Tris pH 7.5 buffer then measurements are carried out by liquid scintillation (Henry I Yamamura, Solomon H. Synder, Proc. Nat. Acad Sc. (1974) 71, No. 5, 1725–1729).

The results are expressed in $IC_{50}$ (concentration necessary to inhibit 50% of the fixed specific radioactivity).

TABLE 1

| Compound of Example | Affinity for the muscarinic receptors $M_1$ and $M_2$ | |
|---|---|---|
| | [$^3H$]pirenzepine | [$^3H$]quinuclidinyl benzylate |
| 1 | 370 | >5000 |
| 2 | 720 | >5000 |
| 3 | 370 | >5000 |
| 4 | 560 | 10000 |
| 5 | 170 | >5000 |
| 6 | 62 | 4500 |
| 7 | 83 | 10000 |

The compounds of Examples 1 to 6 show a remarkable and useful affinity for the muscarinic receptor, and mainly for the $M_1$ type of receptor. On the other hand, the same compounds showed a negligible affinity ($IC_{50}$>5000–10000) for the other receptors examined amongst which there can be cited those of dopamine, histamine, serotonine (5 $HT_1$ and 5 $HT_2$), benzodiazepines, GABA, adrenoreceptors (alpha1, alpha2, beta1, beta2) or also the opiate receptors (mu, kappa).

2) Interaction and Affinity With Different Intestinal Receptors

The interaction of the compounds with different receptors was evaluated on the isolated ileum of a guinea-pig according to the following method.

2.5–3 cm segments of the guinea-pigs, ileum were washed and immediately suspended in a bath containing 10 ml of a Tyrode solution at 37° C. and aerated with a mixture of oxygen (95%) and carbon dioxide (5%). After a stabilization period of at least 30 minutes, the contractions are recorded, maintaining the preparation under constant pressure of 1 g, using a sensor connected to a polygraph. The agonistic action was evaluated by leaving the compound in contact with the isolated tissue for a period needed to give the maximum contraction; then washing was carried out with Tyrode solution. The following dose was only added to the bath after the preparation returned to its base line. Arecoline was used as reference product. The antagonistic action was evaluated on contractions induced by acetylcholine ($1\times10^{-6}M$), histamine ($1\times10^{-5}M$) and barium chloride ($2\times10^{-5}M$). Atropine, diphenydramine and papaverine were used as reference products. The contact time before adding the agonist was one minute.

For each compound the dose-response curves are obtained with 4 to 6 different concentrations and 3 to 5 independent tests. The agonistic activity is expressed by pD$_2$ (negative logarithm of the dose which produces 50% of the maximum effect). The antagonistic activity is expressed by IC$_{50}$ (concentration inhibiting 50% of the maximum response).

The results obtained with the compounds of Examples 1 to 6 are shown in the following Table 2:

TABLE 2

| Compound of Example | Antagonistic to different agents (IC$_{50}$:M) | | | Agonistic action pD$_2$ |
|---|---|---|---|---|
| | ACh | Histam. | BaCl$_2$ | |
| 1 | $8.6 \times 10^{-7}$ | $>10^{-5}$ | $>10^{-5}$ | <4 |
| 2 | $5.5 \times 10^{-6}$ | $>10^{-5}$ | $>10^{-5}$ | <4 |
| 3 | $3.0 \times 10^{-6}$ | $>10^{-5}$ | $>10^{-5}$ | <4 |
| 4 | $1.2 \times 10^{-6}$ | $>10^{-5}$ | $2.5 \times 10^{-6}$ | <4 |
| 5 | $1.4 \times 10^{-6}$ | $>10^{-5}$ | $>10^{-5}$ | <4 |
| 6 | $1.1 \times 10^{-7}$ | $>10^{-5}$ | $2.5 \times 10^{-6}$ | <4 |
| 7 | $5.1 \times 10^{-7}$ | $>10^{-5}$ | $3.6 \times 10^{-6}$ | <4 |
| Atropine | $9.5 \times 10^{-9}$ | | | |
| Diphenydramin | | $8.3 \times 10^{-7}$ | | |
| Papaverine | | | $4.5 \times 10^{-5}$ | |
| Arecoline | | | | 6.68 |

The "in vitro" studies on the isolated guinea-pig ileum revealed that the compounds of the invention are anti-muscarinic agents. They antagonize the contractions induced by acetylchloline but not those induced by histamine.

3) "In Vivo" Anti-Cholinergic Action

The anti-cholinergic activity of the compounds was determined by evaluating the capacity to inhibit the cholino-mimetic effects induced by carbachol. Atropine sulphate was used as reference product.

CD$_1$ male mice weighing 25 to 30 g are used. They are divided into groups of 6 animals and treated by intraperi-toneal route at scalar doses of the products or 0.25% Methocel for the controls. 12 animals are used for each dose. 30 minutes after the administration of the compounds, 1 mg/kg of carbachol, dissolved in physiological serum, was injected into the mice by sub-cutaneous route.

Each animal was examined 30 minutes after the injection of carbachol to evaluate the presence of diarrhoea, salivation and weeping; the body temperature was also measured using a thermocouple inserted 1.5 cm inside the rectum.

Carbochol (1 mg/kg s.c.) induced diarrhoea, salivation and weeping in all the control mice and a decrease of the rectal temperature of about 2.5° C.

For each compound, we have determined the dose which can inhibit, in 50% of the animals, the appearance of cholinomimetic symptoms induced by carbachol and increase the hypothermic effect induced by the cholinergic agent by 1° C.

TABLE 3

| Compound of Example | Dose mg/kg i.p. | | | Body Temperature |
|---|---|---|---|---|
| | Diarrhoea | Salivation | Weeping | |
| 5 | 6 | 50 | >50 | 25 |
| 6 | 12 | >50 | >50 | 50 |
| 7 | 5 | 50 | >50 | 20 |
| Atropine | 0.04 | 0.06 | 0.05 | 0.0.3 |

The results obtained show that, contrary to atropine, the compounds of Example 5, 6 and 7 exert "in vivo" a selective anticholingeric action at the level of the intestinal musculature.

We claim:

1. A compound of formula (I):

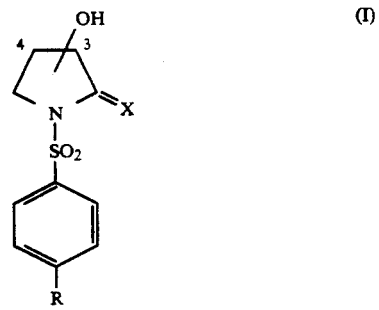

in which
the OH radical is in the 3 or 4 position,
X represents oxygen or sulphur,
R represents a radical

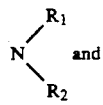

R$_1$ and R$_2$ are identical or different from each other, and each represents a saturated or unsaturated alkyl radical containing up to 8 carbon atoms or form together with the nitrogen atom to which they are linked a heterocyclic radical selected from the group consisting of piperidyl, piperazinyl, hexahydro azepinyl, morpholinyl and pyrrolidinyl;
or a compound of formula (I) having a functional derivative of the hydroxyl in the 3 or 4 position which is metabolized in vivo into the corresponding hydroxylated derivative.

2. The compound of formula (I) as defined in claim 1, in which the hydroxyl radical is in a free form.

3. The compound as defined in claim 1, in which the hydroxyl radical is in the 4 position.

4. The compound as defined in claim 1, in which R$_1$ and R$_2$ form together with the nitrogen atom to which they are linked a heterocyclic radical selected from the group consisting of piperidyl, piperazinyl, hexahydro azepinyl, morpholinyl and pyrrolidinyl.

5. The compound of formula (I) as defined in claim 4, in which the heterocyclic radical is selected from the group consisting of 1-piperidinyl and hexahydro-1H-azepin-1-yl radicals.

6. The compound of formula (I) as defined in claim 1, in which X represents sulphur.

7. The compound of formula (I) as defined in claim 2, in which the hydroxyl radical is in position 4.

8. The compound as defined in claim 2, in which R$_1$ and R$_2$ form together with the nitrogen atom to which they are linked a heterocyclic radical selected from the group consisting of piperidyl, piperazinyl, hexahydro azepinyl, morpholinyl and pyrrolidinyl.

9. The compound as defined in claim 3, in which R$_1$ and R$_2$ form together with the nitrogen atom to which they are linked a heterocyclic radical selected from the group consisting of piperidyl, piperazinyl, hexahydro azepinyl, morpholinyl and pyrrolidinyl.

10. The compound of formula (I) as defined in claim 8, in which X represents sulphur.

11. A compound selected from the group consisting of:

4-hydroxy-1[[4-(1-piperidinyl)-phenyl]-sulphonyl]-2-pyrrolidinethione;

1-[[4-(hexahydro-1H-azepin-1-yl)-phenyl]-sulphonyl]-4-hydroxy-2-pyrrolidinone; and 1-[[4-(hexahydro-1H-azepin-1-yl)-phenyl]-sulphonyl]-4-hydroxy-2-pyrrolidinethione.

12. A pharmaceutical composition for use in treating a patient suffering from muscle spasms comprising an anti-spasmodically effective amount of the compound of claim 1, and an acceptable carrier.

13. A method for treating a patient suffering fom muscle spasms, comprising administering a pharmaceutically effective amount of the compound of claim 1 and a pharmaceutically acceptable carrier.

14. A method for treating a patient suffering from muscle spasms comprising administering a pharmaceutically effective amount of a compound of claim 11 and a pharmaceutically acceptable carrier.

* * * * *